United States Patent [19]

Haag et al.

[11] 4,072,720

[45] Feb. 7, 1978

[54] PRODUCTION OF ALCOHOL

[75] Inventors: Werner O. Haag, Trenton; Darrell Duayne Whitehurst, Titusville, both of N.J.

[73] Assignee: Mobil Oil Corporation, New York, N.Y.

[21] Appl. No.: 414,612

[22] Filed: Nov. 5, 1973

Related U.S. Application Data

[63] Continuation of Ser. No. 107,862, Jan. 19, 1971, abandoned, which is a continuation-in-part of Ser. No. 57,796, July 23, 1970, abandoned, and Ser. No. 672,009, Oct. 2, 1967, abandoned, and Ser. No. 860,807, Sept. 24, 1969, abandoned, which is a continuation-in-part of Ser. No. 672,010, Oct. 2, 1967, abandoned, said Ser. No. 57,796, is a continuation-in-part of Ser. No. 672,008, Oct. 2, 1967, abandoned.

[51] Int. Cl.² .............................................. C07C 29/14
[52] U.S. Cl. ........................... 260/618 H; 252/431 N; 252/431 P; 252/431 R; 260/465.6; 260/617 F; 260/617 C; 260/618 D; 260/613 D; 260/633; 260/635 C
[58] Field of Search ...... 260/638 P, 638 HF, 632 HF, 260/618 D, 618 H, 617 F, 617 C, 465.6, 633, 631.5, 613 D, 635 C

[56] References Cited

U.S. PATENT DOCUMENTS

| 2,754,295 | 7/1956 | Fardig et al. | 260/210 |
| 3,102,150 | 8/1963 | Hunter et al. | 260/638 B |
| 3,352,924 | 11/1967 | Gladrow et al. | 260/638 HF |
| 3,466,340 | 7/1969 | Leach et al. | 260/643 F |
| 3,594,425 | 7/1971 | Brader et al. | 260/632 HF |

FOREIGN PATENT DOCUMENTS

| 1,411,602 | 8/1965 | France | 260/632 HF |

OTHER PUBLICATIONS

Rohm & Haas "Technical Bulletin" (1963), pp. 1–8, Anberlyst XN 1003.

*Primary Examiner*—Joseph E. Evans
*Attorney, Agent, or Firm*—Charles A. Huggett; Michael G. Gilman; Vincent J. Frilette

[57] ABSTRACT

This specification discloses a process for the production of an alcohol by reacting an aldehyde or an acetal with hydrogen in the presence of carbon monoxide, and as a catalyst, an insoluble polymer containing a functional group, which may be an amine, thiol, phosphine, or arsine group, having chemically bonded thereto a metal of Group VIII of the Periodic Table.

20 Claims, No Drawings

PRODUCTION OF ALCOHOL

CROSS REFERENCE TO RELATED APPLICATIONS

This is a continuation, of application Ser. No. 107,862, filed Jan. 19, 1971.

Application Serial No. 107,862, now abandoned, was a continuation-in-part of our copending application, Serial No. 57,796, filed July 23, 1970 and now abandoned. This latter application is a continuation-in-part of our earlier application, Serial No. 672,008, filed October 2, 1967, and now abandoned, which earlier application was copending with said latter application.

Application Serial No. 107,862 was also a continuation-in-part of our then copending application, Serial No. 672,009, filed October 2, 1967 and now abandoned, and our copending application, Serial No. 860,807, filed September 24, 1969 and now abandoned. This latter application was a continuation-in-part of our earlier application, Serial No. 672,010, filed October 2, 1967, and now abandoned, which earlier application was copending with said latter application.

The hydroformylation of olefins to produce alcohols or aldehydes by reacting the olefins with hydrogen and carbon monoxide in the presence of catalysts disclosed in this application is disclosed and claimed in our copending application, Ser. No. 107,863, filed concurrently with application Ser. No. 107,862.

BACKGROUND OF THE INVENTION

1. Field of the Invention

This invention relates to the production of alcohol and relates particularly to the production of alcohol by reacting an aldehyde or an acetal with hydrogen.

2. Description of the Prior Art

The production of an alcohol by reacting an aldehyde with hydrogen is known. The hydrogen adds on to the carbonyl group of the aldehyde to form the hydroxyl group of the alcohol and the reaction is carried out in the presence of a hydrogenation catalyst. Catalysts employed for this purpose have been nickel, the nickel being deposited on kieselguhr, for example, or molybdenum sulfide. Rhodium and cobalt catalysts have also been used. Palladium or platinum deposited on carbon and rhodium deposited on charcoal are also known as catalysts for the hydrogenation of aldehydes. Reaction conditions have included pressures in the range of 2000–4000 pounds per square inch gage and temperatures in the range of 300°–550° F.

The production of an alcohol by reacting an acetal with hydrogen is also known.

In the prior art processes of reacting an aldehyde or an acetal with hydrogen to form an alcohol, various difficulties have been encountered. For example, the selectivity of the catalysts with respect to the reaction of the aldehyde or acetal with the hydrogen, as opposed to competing hydrogenation reactions, has not been all that could be desired. More specifically, where ketones have been in admixture with the aldehyde or acetal, an undesirable, large proportion of the ketones has reacted with the hydrogen in competition with the aldehyde or acetal. Further, more specifically, where the production of an unsaturated alcohol from an unsaturated aldehyde or acetal is desired, hydrogenation of the double bond competes with the hydrogenation of the carbonyl groups of the aldehyde or acetal with the result that an unsaturated alcohol is not formed. Moreover, hydrogenolysis of the hydroxyl group of the alcohol product can also occur to an undesired extent.

Another difficulty, with respect to various of the processes heretofore employed, is the tendency of the catalysts to lose activity to a greater or lesser extent in the presence of various impurities in the aldehyde or acetal feed. Thus, for example, rhodium deposited on charcoal is almost completely inhibited in its hydrogenation activity for aldehydes in the presence of carbon monoxide. A commercial source of aldehydes is the hydroformylation of olefins by reacting the olefins with carbon monoxide and hydrogen in the presence of a catalyst. Accordingly, where the aldehyde feed has been obtained by hydroformylation of olefins, rigorous cleanup procedures are required to remove traces of carbon monoxide from the feed in order to prevent catalyst deactivation. Further, for example, various of the catalysts heretofore employed are deactivated by dienes and sulfur in the feed and, where such catalysts have been employed, purification of a feed containing such compounds has been required.

SUMMARY OF THE INVENTION

In accordance with the invention, there is provided a process for the production of an alcohol. An aldehyde or an acetal is reacted with hydrogen in the presence of carbon monoxide and a catalyst. The catalyst is characterized as being an insoluble polymer containing a functional group having chemically bonded thereto a metal of Group VIII of the Periodic Table.

DESCRIPTION OF THE PREFERRED EMBODIMENTS

In the process of the invention, the catalyst is essentially insoluble in the reaction mixture. The metal portion of the catalyst is chemically bonded to the polymer portion. Being chemically bonded to the polymer portion, the metal portion is strongly bonded to the polymer portion. These bonds are not readily severed and the metal readily resists solution in the reaction mixture. Moreover, the polymer portion of the catalyst is insoluble. By "insoluble" is meant that the polymer is insoluble in common solvents and, in particular, is insoluble in the reactants and reaction products in the reaction mixture. The catalysts, therefore, can be used in liquid phase operations for long periods of times.

The process of the invention provides other advantages. For example, in the process of the invention, there is a selective production of alcohols. The predominant reaction is the conversion of aldehydes and acetals to alcohols with competing reactions involving the hydrogen being at a minimum. Thus, where ketones are contained in the aldehyde or acetal feed, hydrogenation of the ketones is relatively insignificant. Further, in the reaction of an unsaturated aldehyde with hydrogen, the conversion of the carbonyl group to a hydroxyl group is the predominant reaction with hydrogenation of the double bond of the unsaturated aldehyde being at a minimum. Furthermore, hydrogenolysis of the hydroxyl group of the alcohol is insignificant.

Another advantage of the process of the invention arises from the relative insensitivity of the catalyst to impurities in the aldehyde or acetal feed. The activity of the catalyst is not inhibited by carbon monoxide. Thus, aldehydes obtained by hydroformylation of olefins with carbon monoxide and hydrogen can be employed without purification to rid the feed of carbon monoxide. Further, synthesis gas, obtained by steam reforming of methane and containing substantial quantities of carbon monoxide in addition to hydrogen, may be employed, without purification to remove the carbon monoxide, as the source of hydrogen for the reaction. The catalyst is not deactivated by dienes and small amounts of sulfur compounds. Thus, purification of a feed to rid it of dienes and sulfur compounds is not required.

The polymer portion of the catalyst may be provided by any solid insoluble polymer capable of containing a functional group. Preferably, the polymer is an organic polymer. Suitable polymers include copolymers such as those of styrene and a divinylbenzene compound, for example, a styrene-divinylbenzene copolymer. Other suitable polymers include resins such as phenol-aldehyde, for example, phenol-formaldehyde, melamine-formaldehyde, urea-formaldehyde, polyalkylene-formaldehyde, and polystyrene resins. Cellulose polymers can also be used. It is preferred that the organic portion of the polymer be intrinsically porous.

Functional groups contained by the polymer portion of the catalyst include amine, thiol, phosphine, or arsine groups. Preferred groups are tertiary amine groups. The tertiary amine groups may be monoamine, diamine, or triamine groups. The nitrogen atom in these amine groups may be substituted with aromatic or aliphatic groups or it may be part of a heterocyclic ring system such as pyridine, quinoline, thiazoles, diazoles, triazoles, oxazoles, pyrimidine, imidazole, purine, methylindole, pyrazine, adenine, and uracil. Tertiary amine groups containing at least one, and preferably two, aliphatic alkyl groups are preferred. Particularly preferred tertiary amine functional groups are those whose soluble analogs have a base strength measured as $pK_b$ of from 3 to 7.

The attachment of the functional group to the polymer is a conventional procedure. Accordingly, a detailed discussion of the procedure is not believed necessary. However, it may be stated that these procedures involve appropriate chemical treatment of the polymer. For example, a styrenedivinylbenzene copolymer may have an amine functional group attached thereto by first chloromethylating the polymer and subsequently reacting it with the amine. The resulting product comprises the polymer with the nitrogen of the amine chemically bound to a carbon atom of a benzene ring of the polymer. Further, for example, a styrene-divinylbenzene copolymer containing a phosphine functional group may be obtained by reacting the copolymer with phosphorus trichloride. The phosphorus chemically binds to a carbon atom of a benzene ring of the copolymer. The copolymer may be subjected to further chemical action to substitute an organic radical for the remaining chlorine atoms attached to the phosphorus.

The metal portion of the catalyst may be any metal of Group VIII of the Periodic Table. These metals are iron, cobalt, nickel, ruthenium, rhodium, palladium, osmium, iridium, and platinum. Preferred metals are cobalt, ruthenium, and rhodium. Rhodium is particularly preferred.

The metal portion of the catalyst is bonded to the functional group. Procedures for bonding are disclosed in the aforementioned applications, Ser. Nos. 672,009 and 860,807. These procedures include reacting the polymer containing the functional group with a complex compound of the metal, the complex compound comprising the metal and at least two ligands. One of the ligands exchanges with the polymer containing the functional group, i.e., ligand exchange, thereby chemically bonding the metal polymer through the functional group.

Various types of aldehyde may be employed to form an alcohol by the process of the invention. The aldehyde may be an open chain or a cyclic aldehyde. For example, aldehydes which may be hydrogenated include saturated linear aldehydes, branched chain aldehydes, cyclic aldehydes such as monocyclic, bicyclic, tricyclic and other cyclic aldehydes, and aromatic aldehydes. Further, for example, aldehydes which may be employed include unsaturated aldehydes and these may have more than one double bond. The aldehyde may also be substituted. Specific aldehydes include heptanal, crotonaldehyde, benzaldehyde, n-butyraldehyde, isobutyraldehyde, 2-ethyl-hexenal, tridecyl aldehyde, cyclohexyl carboxaldehyde, dicyclopentenecarboxaldehyde, 3-cyano-propionaldehyde, p-chlorobenzaldehyde, and 3-chloropropionaldehyde. The aldehyde employed may be in a substantially pure state or may be in a mixture with a component other than an aldehyde. Further, a mixture of aldehydes may be employed.

The aldehyde or mixture of aldehydes employed may be obtained by reacting an olefin with hydrogen and carbon monoxide, i.e., by hydroformylation. The entire product of the hydroformylation reaction may be employed or only a portion of the product may be employed. Thus, the aldehyde or aldehydes, or a portion thereof, may be separated from the hydroformylation reaction product and subjected to the hydrogenation reaction. For the purpose of providing an aldehyde feed, any conventional hydroformylation procedure may be employed.

The aldehyde or mixture of aldehydes employed may also be obtained by other procedures. Thus, the aldehyde or mixture of aldehydes may be obtained by oxidation of olefins such as ethylene.

The aldehyde employed may also be a natural compound such as vanillin, citral, citronellal, and cinnamaldehyde.

Various types of acetal, also, may be hydrogenated to form an alcohol by the process of the invention. The term "acetal" is intended to include the compounds known as hemiacetals. The acetals have the formula:

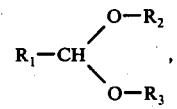

wherein each of $R_1$, $R_2$ and $R_3$ can be an alkyl or aryl group such as a methyl, ethyl, propyl, butyl, allyl, benzyl, or phenyl group or may be a substituted alkyl or aryl group where the substituent is oxygen, nitrogen, sulfur, or a halogen. Each of $R_1$, $R_2$ and $R_3$ may be the same or may be different. The acetals may be cyclic, or acyclic, substituted or unsubstituted. Specific acetals include acetals corresponding to the specific aldehydes mentioned above. For example, the acetal may be the dimethyl acetal of heptanal. Other acetals include naturally occurring compounds such as glucose and other sugars. The acetals employed may also be obtained by hydroformylation of an olefin, acetals as well as aldehydes being produced in this reaction. Mixtures of acetals may also be employed.

With the catalyst employed in the process of the invention, the hydrogenation reaction requires the presence of carbon monoxide. In the absence of carbon monoxide, the hydrogenation reaction occurs only slowly or at very high temperatures. The amount of carbon monoxide may be such that the ratio of hydrogen to carbon monoxide is from about 0.1 to 20.

With respect to the hydrogenation reaction, the conditions for optimum hydrogenation will vary somewhat depending upon the aldehyde or acetal employed. The amount of hydrogen employed may be from 1 to 20 moles of hydrogen per mole of aldehyde or acetal. In a continuous process, the aldehyde feed may be passed through a bed of the catalyst at a liquid hourly space velocity (LHSV) from 0.1 to 10 volumes of aldehyde feed per volume of catalyst per hour. Temperatures of hydrogenation may be from 50° to 250° C. Pressures employed may be from 5 to 300 atmospheres.

It has been found to be particularly effective to employ an added solvent in the reaction mixture for the hydrogenation of the aldehydes and acetals. Marked increases in the rates of alcohol formation are encountered depending upon the type of solvent employed. In some cases, increases in the rate of alcohol formation by a factor of 100 can be obtained. The magnitude of the rate enhancement is a function, however, of the catalyst and the nature of the solvent.

Solvents that may be employed include aromatic hydrocarbons, ethers, esters, ketones, nitriles, amines, phenols, hydroxylamines, sulfones, carboxylic acids, phosphorus- and sulfur-containing acids, alcohols, and water. Preferred solvents are those containing hydroxyl groups. Especially preferred solvents are water and alcohols. The alcohols may be primary, secondary, or tertiary and may be substituted or unsubstituted. The substituents may be hydrocarbons, halides, amines, sulfides, ethers, esters, carboxylic acids and others. Lower molecular weight alcohols are more effective than higher molecular weight alcohols. Specific solvents that may be employed include isobutyl alcohol, butyl ether, benzene, triethylamine, acetonitrile, 3-pentanone, methanol, hexanol, and acetic acid. The choice of a particular solvent is determined, among other factors, by its effectiveness to bring about a desired rate enhancement. Its choice is also determined by the ease with which it can be recovered from the reaction products. Thus, it is preferred to employ a solvent which has a boiling point below the alcohol product so that it may be separated from the reaction products simply by distillation. The alcohol product can be used as the solvent. Water as an added solvent has the special advantage of easy separation from the reaction products where these are not miscible with water to any extent.

The concentration of the added solvent in the reaction mixture will affect the rate of the hydrogenation reaction. However, a leveling effect occurs in some cases. Major activity increases occur up to about 6 to 10 volume percent where the solvent is an alcohol. Concentrations greater than this, while giving activity increases, give proportionally smaller increases. However, large concentrations of alcohols do not harm the overall catalyst performance and may be desirable to aid in heat removal.

The use of an added solvent has another advantage. As mentioned previously, it is preferred that the polymer portion of the catalyst be intrinsically porous. Porosity of the polymer portion of the catalyst imparts increased activity to the catalyst. With catalysts having an organic polymer portion which is not intrinsically porous, porosity may be induced into the polymer portion by solvent swelling. Various of the solvents mentioned above will effect swelling of the polymer portion of the catalysts. These solvents include the alcohols such as methanol, ethanol, isopropanol, isobutanol, and the dialcohols such as ethylene glycol. The increased activity of the catalyst achieved from swelling of the polymer portion of the catalyst will be a function of a number of variables including the degree of swelling.

It is a particular feature of the catalyst employed in the process of the invention that it is relatively unaffected by various impurities that may be found in the aldehyde or acetal feed. These impurities include dienes and sulfur compounds and their removal has been heretofore necessary before hydrogenation of the aldehyde or acetal feed with certain catalysts could be carried out. On the other hand, the catalyst employed in the process of the invention is not affected by dienes. Further, the presence of small amounts of sulphur compounds in the feed has little or no effect on the rate of hydrogenation or on the lifetime of the catalyst. Other impurities that may be in the aldehyde or acetal feed, such as phenols and nitrogen and phosphorous compounds, have no deleterious effect on the catalyst. Further, these compounds are not hydrogenated in the presence of the catalyst.

The following examples will be illustrative of the invention.

EXAMPLE 1

This example will illustrate the preparation of a catalyst comprising rhodium bound to a styrene-divinylbenzene copolymer containing benzyldimethylamine functional groups.

Rhodium trichloride ($RhCl_3 \cdot 3H_2O$) in the amount of 10.3 g (grams) was dissolved along with 12 g of sodium chloride in 1700 ml (milliliters) of water. To this solution were added 200 g of 18–50 mesh amine resin consisting of intrinsically porous cross-linked styrene-divinylbenzene copolymer containing benzyldimethylamine functional groups. This mixture was stirred for 16 hours at 50° C., during which time the solution became colorless. The mixture was then cooled and the resultant solid catalyst was removed by filtration. The catalyst was then washed successively with water, methanol, and benzene, and dried on a rotary evaporator in vacuo at 50° C. Analysis showed the catalyst to contain, on a weight basis, 1.42% of rhodium, 2.23% of chlorine, and 0.03% of sodium.

EXAMPLE 2

This example will illustrate the preparation of a catalyst comprising rhodium bound to an acrylic polymer containing tertiary amine functional groups.

Rhodium trichloride ($RhCl_3 \cdot 3H_2O$) in the amount of 15 g along with 18 g of sodium chloride were dissolved in 200 ml of water. To this solution were added 300 g of an organic polymer suspended in 2000 ml of water. This polymer was a gel-type acrylic polymer containing tertiary amine functional groups. The resultant suspension was stirred, heated at 50° C. for 24 hours, and left at ambient temperature for 3 days. The resultant solid catalyst was removed from the suspension by filtration, chromatographically washed with water, methanol, and benzene, and then dried in a rotary evaporator in vacuo. The yield of dry catalyst was 305.5 g and contained, on a weight basis, 1.96% of rhodium, 2.34% of chlorine, and 0.01% of sodium.

EXAMPLE 3

This example will illustrate the preparation of a catalyst comprising rhodium bound to a styrene polymer containing N,N,N'trimethyl N'benzylethylenediamine functional groups.

An organic polymer containing N,N,N'trimethyl N'benzylethylenediamine functional groups was prepared. In the preparation, 50 g of an intrinsically porous cross-linked polymer of styrene containing N-benzylethylenediamine functional groups were suspended in 510 g of formic acid and 276 g of 36% aqueous formaldehyde. The resultant suspension was stirred and heated to the reflux temperature and maintained at this temperature for 24 hours. The suspension was cooled and the solid polymer removed by filtration. The polymer was then washed with the following sequence of solvents: water, 2N (Normal) aqueous sodium hydroxide solution, water, methanol, and benzene. The washed polymer was dried using a rotary evaporator. The dried material contained, on a weight basis, 75.3% of carbon, 8.5% of hydrogen, and 7.6% of nitrogen.

The dried polymer, in the amount of 15 g, was suspended in 200 ml of water containing 0.772 g of rhodium trichloride ($RhCl_3 \cdot 3H_2O$) and 0.9 g of sodium chloride. The resultant suspension was stirred and heated to 50°–55° C. and maintained at this temperature for about 21 hours after which it was allowed to cool to room temperature. The resultant catalyst was removed by filtration and washed sequentially with water, methanol, and benzene. The catalyst was then dried in a vacuum oven at 100° C. The catalyst weighed 16.2 g and contained, on a weight basis, 1.33% of rhodium, 1.53% of chlorine, and 0.25% of sodium.

EXAMPLE 4

In this example, a catalyst was prepared in which ruthenium was bound to an amine-containing styrene-divinylbenzene copolymer.

Fifty g of an intrinsically porous organic polymer composed of cross-linked styrene-divinylbenzene containing benzyldimethylamine functional groups were added to a solution of 2.0 g of triruthenium dodecacarbonyl dissolved in 500 ml of benzene. The resultant suspension was heated to the reflux temperature and maintained at this temperature for about 4 hours. During this time, evolution of carbon monoxide was noted. The catalyst was isolated by filtration, washed with 1 liter of benzene, and dried in a vacuum oven at 110° C. The resultant catalyst had about 2%, by weight, ruthenium chemically bound to the amine groups of the polymer.

EXAMPLE 5

This example will illustrate the preparation of a catalyst comprising rhodium bound to an ion exchange cellulose containing tertiary amine functional groups.

Rhodium carbonyl chloride ($Rh_2(CO)_4Cl_2$) in the amount of 0.1887 g was dissolved in 200 ml of benzene and the resulting solution was contacted with 10 g of a commercially available, weakly basic, ion exchange cellulose identified as DEAE Cellulose. The mixture was stirred at room temperature until it became colorless. The benzene solvent was then removed by evaporation in vacuo. The resultant catalyst was composed of rhodium carbonyl chloride chemically bound to the tertiary amine functional groups of the ion exchange cellulose. This catalyst contained, on a weight basis, 43.6% of carbon, 7.1% of hydrogen, 0.58% of rhodium, and 0.36% of chlorine.

EXAMPLE 6

This example will be illustrative of the process of the invention for producing alcohol from aldehydes. It will be also illustrative of the fact that carbon monoxide is required in order to effect hydrogenation of an aldehyde.

In this example, the catalyst of Example 1 was employed. This catalyst, in the amount of 3 g, was placed in an autoclave with 25 ml of heptanal and 75 ml of methylcyclohexane solvent. The contents of the autoclave were stirred, heated to 100° C., and hydrogen was added to give a total pressure of 800 psig (pounds per square inch gage). After 60 minutes, a sample aliquot of the reaction mixture was withdrawn from the autoclave and analyzed by vapor phase chromatography. Analysis showed that no reaction had occurred during this time. After 90 minutes, carbon monoxide was added to the autoclave to give a total pressure of 1010 psig. An immediate, rapid uptake of gas took place and after an additional 167 minutes a sample aliquot was withdrawn and analyzed by vapor phase chromatography. This analysis showed that 6.3% of the heptanal had been reduced to heptanol.

The reaction was allowed to continue and after 17 hours about 35% of the heptanal was converted to heptanol. After a total reaction time of 67 hours, 75% of the heptanal had been converted to heptanol. After a total reaction time of 68 hours, an additional 300 psig of carbon monoxide were introduced into the autoclave whereupon the rate of gas uptake increased rapidly. After another 1.3 hours, at this higher carbon monoxide pressure, reaction time, 97% of the heptanal had been converted to heptanol.

For purposes of comparison, the procedure of this example was carried out employing a conventional rhodium catalyst under identical reaction conditions. An autoclave was charged with 1 g of 5% rhodium on charcoal catalyst, 25 ml of heptanal, and 75 ml of methylcyclohexane solvent. The contents of the autoclave were stirred and heated to 100° C. and hydrogen was added to give a total pressure of 810 psig. An immediate absorption of gas took place. After 60 minutes, a sample aliquot was withdrawn from the autoclave and analyzed by vapor phase chromatography. This analysis showed that about 1.2% of the heptanal had been hydrogenated to heptanol. After a total reaction time of 90 minutes, carbon monoxide was added to the autoclave to produce a total pressure of 1010 psig. On the addition of carbon monoxide, the gas absorption essentially stopped. After a total reaction time of 17 hours, a sample aliquot was withdrawn from the autoclave and analyzed by vapor phase chromatography. This analysis showed that only 2% of the heptanal had been converted to heptanol. Thus, this catalyst induced a slow aldehyde hydrogenation with hydrogen alone and was almost completely inhibited by the presence of the carbon monoxide.

EXAMPLE 7

This example will illustrate the hydrogenation of an aromatic aldehyde.

An autoclave was charged with 2 g of the catalyst of Example 1, 25 ml of benzaldehyde, and 75 ml of cyclohexane solvent. The contents of the autoclave were stirred and heated to 207° F. under an atmosphere of carbon monoxide. The carbon monoxide was introduced into the autoclave to produce a pressure of 530 psig. Hydrogen was then added to the autoclave to produce a total pressure of 1030 psig and the reaction began. The pressure in the autoclave was maintained between 835 and 104 psig by periodic addition of hydrogen. After 19.4 hours, the autoclave was cooled and the contents removed.

Analysis of the product removed from the autoclave showed that 99% of the benzaldehyde had been converted to benzyl alcohol. On the other hand, less than 0.3% of the benzaldehyde was converted to toluene. Thus, by the process of the invention, an aromatic aldehyde can be converted to an alcohol with essentially no hydrogenolysis of the aromatic alcohol obtained as a reaction product.

EXAMPLE 8

This example will be illustrative of the production of alcohols from aldehydes and acetals produced from the reaction of an olefin with hydrogen and carbon monoxide.

An autoclave was charged with 2 g of the catalyst of Example 1, 90 ml of 1-hexane, and 10 ml of methanol. The contents of the autoclave were stirred and heated to 100° C. under an atomosphere of carbon monoxide. An equimolar mixture of hydrogen and carbon monoxide was then introduced into the autoclave to produce a total pressure of 1015 psig and the reaction began. The pressure was maintained between 695 and 1000 psig by periodic addition of an equimolar mixture of carbon monoxide and hydrogen. Samples were taken periodically and analyzed by vapor phase chromatography. The results of these analyses are presented in the following table.

TABLE I

|  | Reaction Time (hours) | | |
| --- | --- | --- | --- |
|  | 1.1 | 6.0 | 21.5 |
| Isomeric hexenes | 64.3 | 23.6 | 6.3 |
| Isomeric heptanals | 28.2 | 42.7 | 7.5 |
| Isomeric heptanal methyl acetals | 6.4 | 0.8 | 0.4 |
| Isomeric heptyl alcohols | 1.2 | 32.9 | 85.8 |

The values for the components listed in the table represent the molar percent composition of the reaction mixture normalized to a methanol free basis.

It will be seen that the aldehydes and acetals formed by the reaction of the 1-hexene with the carbon monoxide and hydrogen in the early stages of the reaction were converted to alcohols.

EXAMPLE 9

The following example illustrates the selective reaction of aldehydes in the presence of ketones.

An autoclave was charged with 2 g of the catalyst of Example 1, 25 ml of 3-pentanone, 7 ml of heptanal, and 100 ml of cyclohexane solvent. The contents of the autoclave were stirred and heated to 210° F. under an atmosphere of carbon monoxide. Carbon monoxide was introduced into the autoclave to give a pressure of 500 psig. Hydrogen was then added to give a total pressure of 1150 psig and the reaction began. After 19 hours, the pressure had dropped to 990 psig. A sample aliquot was withdrawn from the autoclave and analyzed by vapor phase chromatography. This analysis showed that 88% of the heptanal had been converted to heptanol whereas only 0.6% of the 3-pentanone had been converted to 3-pentanol.

EXAMPLE 10

In this example, for comparison with Example 9, a conventional catalyst was used in the competitive hydrogenation of a mixture of an aldehyde and a ketone.

An autoclave was charged with 3 g of a nickel-on-kieselguhr catalyst (identified commercially as Harshaw Ni-0104P), 7 ml of heptanal, 25 ml of 3-pentanone, and 100 ml of cyclohexane solvent. The contents of the autoclave were stirred and heated to 211° F. Hydrogen was introduced into the autoclave to give a total pressure of 1000 psig and the reaction began. After 1 hour, a sample aliquot was withdrawn from the autoclave and analyzed by vapor phase chromatography. This analysis showed that 77% of the heptanal had been converted to heptanol and 4.3% of the 3-pentanone had been converted to 3-pentanol. Thus, the nickel catalyst was much less selective for the preferential hydrogenation of aldehydes in mixtures containing both aldehydes and ketones.

EXAMPLE 11

This example will illustrate the highly selective nature of the process of the invention for the hydrogenation of aldehydes as compared with attempted hydrogenations of a number of different types of potentially reducible organic compounds.

In each of the eight reactions an autoclave was charged with catalyst and the compound to be reduced. In all of the reactions but the last two, the autoclave was also charged with a solvent, namely, cyclohexane in the amount of 100 ml. In the seventh reaction, two potentially reducible organic compounds were employed together. The catalysts employed were those prepared by Examples Nos. 1, 2, and 4. The contents of the autoclaves were stirred and heated to 100±2° C. under an atmosphere of carbon monoxide. An equimolar mixture of carbon monoxide and hydrogen was then added to the autoclave to produce a total pressure of 1050 ± 50 psig. After the given reaction time, a sample aliquot of the reaction mixture was withdrawn and analyzed by vapor phase chromatography.

The table gives the class of the organic compound, the organic compound and its amount, the amount of catalyst, the number of the example herein by which the catalyst was prepared, the reaction time, and the extent of conversion.

TABLE II

| Compound Class | Compound | Amount (ml) | Amount of Catalyst (g) | Catalyst Prepared by Example No. | Reaction Time - hours | Mole % Conversion |
| --- | --- | --- | --- | --- | --- | --- |
| aldehyde | heptanal | 7 | 2 | 1 | 19 | 88 |
| ketone | 3-pentanone | 25 | 2 | 1 | 19 | 0.6 |
| ester | ethyl acetate | 25 | 2 | 1 | 67 | No reaction observed |
| formyl ester | methyl formate | 25 | 2 | 1 | 67 | " |
| formyl ester | butyl formate | 25 | 2 | 4 | 16.5 | " |
| amide | N,N-dimethyl formamide | 25 | 2 | 4 | 23 | " |
| nitrile | acetonitrile | 25 | 2 | 2 | 19 | " |

TABLE II-continued

| Compound Class | Compound | Amount (ml) | Amount of Catalyst (g) | Catalyst Prepared by Example No. | Reaction Time - hours | Mole % Conversion |
|---|---|---|---|---|---|---|
| and aromatic lactone | and benzene gamma-valerolactone | 75 100 | 5 | 1 | 27 | " |

EXAMPLE 12

This example will illustrate the hydrogenation of an unsaturated aldehyde to produce an unsaturated alcohol.

An autoclave was charged with 2 g of a catalyst prepared according to the procedure of Example 1 and 100 ml of crotonaldehyde. The contents of the autoclave were stirred and heated to 209° F. under an atmosphere of carbon monoxide. An equimolar mixture of carbon monoxide and hydrogen was added to the autoclave to produce a total pressure of 1000 psig and the reaction began. The pressure was maintained between 890 and 1075 psig by periodic addition of the carbon monoxide-hydrogen mixture. After 21 hours, a sample aliquot was withdrawn from the autoclave and analyzed by vapor phase chromatography. This analysis showed that the reaction mixture was composed of 59% of unreacted crotonaldehyde, 32% of butyraldehyde, 3% of butanol, and 4% of butenol. Thus, whereas a considerable portion of the crotonaldehyde was hydrogenated at the double bond to produce butyraldehyde, and some of the butyraldehyde was hydrogenated to butanol, a significant portion of unsaturated alcohols, i.e., butenols, were produced.

EXAMPLE 13

This example will further illustrate the production of alcohols from aldehydes obtained by reaction of an olefin with carbon monoxide and hydrogen.

The catalyst of Example 5 was used. An autoclave was charged with 3.0 g of the catalyst, 10 ml of 1-hexene, 10 ml of methanol, and 80 ml of benzene solvent. The contents of the autoclave were stirred and heated to 100° C. under an atmosphere of carbon monoxide. An equimolar mixture of carbon monoxide and hydrogen was added to the autoclave to give a total pressure of 1005 psig and the reaction began. The pressure of the autoclave was maintained between 900 and 1020 psig by periodic addition of the carbon monoxide-hydrogen mixture. After about 1 hour, a sample aliquot was withdrawn and analyzed by vapor phase chromatography. This analysis showed that essentially all of the 1-hexene had been converted to a mixture of 2- and 3-hexenes (52% of 1-hexene product) and isomeric heptyl aldehydes (48% of 1-hexene product).

After about 19 hours, another sample was withdrawn and analyzed. This analysis showed that the product composition was as follows: 0.3% hexenes, 18.6% heptyl aldehydes, and 81.1% heptyl alcohols. Thus, a considerable portion of the heptyl aldehydes produced by the reaction of the olefin with the carbon monoxide and hydrogen was converted to alcohols.

EXAMPLE 14

This example will illustrate the production of an alcohol from an acetal.

An aqueous solution of glucose is made by dissolving 50 g of glucose in 100 ml of water. The dissolved glucose is reduced to sorbitol using the procedure of Example 8 and 2 g of the catalyst of Example 1. On addition of the hydrogen-carbon monoxide mixture, a rapid absorption of gas is noted and glucose is converted to sorbitol with high selectivity.

We claim:

1. A process for producing alcohols comprising reacting a reducible aldehyde or an acetal thereof, said aldehyde having about 3 to 13 carbon atoms, corresponding to said alcohol with about 1 to 20 moles of hydrogen per mole of aldehyde or acetal, in the presence of about 0.1 to 20 moles of carbon monoxide per mole of hydrogen at about 50° to 250° C in contact with an intrinsically porous catalyst which is essentially insoluble in the reaction mixture comprising said aldehyde or acetal and the reaction products thereof with hydrogen, which catalyst comprises an organic polymer selected from the group consisting of cellulose, poly(styrene-divinyl benzene), poly(phenol-formaldehyde), poly(melamine-formaldehyde), poly(ureaformaldehyde), poly(alkylene-formaldehyde) and polystyrene having a tertiary amine having a $pK_b$ of 3 to 7 and containing at least one alkyl substituent bonded thereto; and having a metal moiety selected from the group consisting of cobalt, rhodium and ruthenium bonded to said amine.

2. The process of claim 1 wherein said metal is rhodium.

3. The process of claim 1 wherein said metal is cobalt.

4. The process of claim 1 wherein said metal is ruthenium.

5. The process of claim 1 wherein said alcohol is an unsaturated alcohol and said aldehyde or acetal is an unsaturated aldehyde or acetal.

6. The process of claim 5 wherein said unsaturated aldehyde is crotonaldehyde.

7. The process of claim 1 wherein said aldehyde is obtained by hydroformylation of an olefin in the presence of a catalyst.

8. The process of claim 1 wherein said aldehyde is mixed with a polar solvent during reaction with said hydrogen and carbon monoxide.

9. The process of claim 8 wherein said polar solvent is an alcohol.

10. The process of claim 1 wherein said organic polymer is a divinylbenzene polymer.

11. The process of claim 1 wherein said organic polymer is a styrene-divinylbenzene copolymer and said amine functional group is an N,N,N'trimethyl N'benzylethylenediamine functional group.

12. The process of claim 1 wherein said aldehyde or acetal is reacted with said hydrogen in the presence of said carbon monoxide and said catalyst by passing said aldehyde or said acetal through a bed of said catalyst at a liquid hourly spaced velocity from 0.1 to 10.

13. The process of claim 1 wherein said aldehyde is benzaldehyde.

14. The process of claim 1 wherein said aldehyde is heptanal, said organic polymer is styrene-divinylbenzene copolymer, said functional group is benzyldimethylamine, and said metal is rhodium.

15. The process of claim 1 wherein said aldehyde is benzaldehyde, said organic polymer is styrene-divinylbenzene copolymer, said functional group is benzyldimethylamine, and said metal is rhodium.

16. The process of claim 1 wherein said aldehyde is crotonaldehyde, said organic polymer is styrene-divinylbenzene copolymer, said functional group is benzyldimethylamine, and said metal is rhodium.

17. The process of claim 1 wherein said acetal is glucose, said organic polymer is styrene-divinylbenzene copolymer, said functional group is benzyldimethylamine, and said metal is rhodium.

18. The process of claim 1 wherein said aldehyde is heptanal, said ketone is 3-pentanone, said organic polymer is styrene-divinylbenzene copolymer, said functional group is benzyldimethylamine, and said metal is rhodium.

19. A process as claimed in claim 1 wherein said aldehyde or acetal has a ketone admixed therewith.

20. The process of claim 19 wherein said aldehyde is heptanal and said ketone is 3-pentanone.

* * * * *

UNITED STATES PATENT AND TRADEMARK OFFICE
CERTIFICATE OF CORRECTION

PATENT NO. : 4,072,720
DATED : February 7, 1978
INVENTOR(S) : Werner O. Haag and Darrell Duayne Whitehurst It is certified that error appears in the above-identified patent and that said Letters Patent are hereby corrected as shown below:

Column 9, line 6        "104 psig" should be -- 1040 psig --

Signed and Sealed this

Twenty-third Day of May 1978

[SEAL]

Attest:

RUTH C. MASON
Attesting Officer

LUTRELLE F. PARKER
Acting Commissioner of Patents and Trademarks